United States Patent
Greene et al.

(10) Patent No.: US 10,570,468 B2
(45) Date of Patent: Feb. 25, 2020

(54) CRYSTALLIZED OXALATE DECARBOXYLASE AND METHODS OF USE

(71) Applicant: Allena Pharmaceuticals, Inc., Newton, MA (US)

(72) Inventors: Jack Greene, Allston, MA (US); Richard Johnson, West Bridgford (GB); Dennis Krushinskie, South Grafton, MA (US); Bhami Shenoy, South Grafton, MA (US)

(73) Assignee: Allena Pharmaceuticals, Inc., Newton, MA (US)

( * ) Notice: Subject to any disclaimer, the term of this patent is extended or adjusted under 35 U.S.C. 154(b) by 0 days.

(21) Appl. No.: 16/275,734

(22) Filed: Feb. 14, 2019

(65) Prior Publication Data

US 2020/0024673 A1    Jan. 23, 2020

Related U.S. Application Data

(63) Continuation of application No. 15/630,978, filed on Jun. 23, 2017, now Pat. No. 10,246,755, which is a continuation of application No. 14/761,521, filed as application No. PCT/US2014/012008 on Jan. 17, 2014, now Pat. No. 9,714,456.

(60) Provisional application No. 61/754,342, filed on Jan. 18, 2013.

(51) Int. Cl.
| | |
|---|---|
| *A61K 9/16* | (2006.01) |
| *A61K 38/51* | (2006.01) |
| *C12N 9/88* | (2006.01) |
| *C12N 9/16* | (2006.01) |
| *A61K 38/00* | (2006.01) |

(52) U.S. Cl.
CPC .... *C12Y 401/01002* (2013.01); *A61K 9/1623* (2013.01); *A61K 9/1635* (2013.01); *A61K 9/1647* (2013.01); *A61K 9/1652* (2013.01); *A61K 38/51* (2013.01); *C12N 9/88* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 5,866,778 A | 2/1999 | Hartman et al. | |
| 5,976,529 A | 11/1999 | Navia et al. | |
| 6,140,475 A | 10/2000 | Margolin et al. | |
| 6,218,134 B1 | 4/2001 | Yamauchi et al. | |
| 6,229,065 B1 | 5/2001 | Freyssinet et al. | |
| 6,235,530 B1 | 5/2001 | Freyssinet et al. | |
| 6,281,252 B1 | 8/2001 | Holmes-Farley et al. | |
| 6,503,307 B1 | 1/2003 | Noguchi | |
| 6,503,507 B1 | 1/2003 | Allen | |
| 6,541,606 B2 | 4/2003 | Margolin et al. | |
| 6,929,940 B1 | 8/2005 | Richards et al. | |
| 8,142,775 B2 | 3/2012 | Shenoy et al. | |
| 8,431,122 B2 | 4/2013 | Sidhu et al. | |
| 8,741,284 B2 | 6/2014 | Shenoy et al. | |
| 9,155,785 B2 | 10/2015 | Shenoy et al. | |
| 9,714,456 B2 | 7/2017 | Greene et al. | |
| 9,821,041 B2 | 11/2017 | Shenoy et al. | |
| 10,246,755 B2 | 4/2019 | Greene et al. | |
| 10,369,203 B2 | 8/2019 | Shenoy et al. | |
| 2003/0113308 A1 | 6/2003 | Sidhu | |
| 2004/0234514 A1 | 11/2004 | Sidhu | |
| 2005/0232901 A1 | 10/2005 | Zaghmout | |
| 2006/0104935 A1 | 5/2006 | Margolin et al. | |
| 2007/0178070 A1 | 8/2007 | Kaul et al. | |
| 2007/0184118 A1 | 8/2007 | Li et al. | |
| 2008/0038246 A1 | 2/2008 | Shenoy et al. | |
| 2008/0311101 A1 | 12/2008 | Shenoy et al. | |
| 2012/0189604 A1* | 7/2012 | Sidhu | C07K 1/14 424/94.5 |
| 2012/0308545 A1 | 12/2012 | Shenoy et al. | |
| 2013/0108607 A1 | 5/2013 | Cowley et al. | |
| 2016/0051647 A1 | 2/2016 | Shenoy et al. | |
| 2016/0144094 A1 | 5/2016 | Margolin et al. | |
| 2018/0214522 A1 | 8/2018 | Shenoy et al. | |
| 2018/0250371 A1 | 9/2018 | Shenoy et al. | |

FOREIGN PATENT DOCUMENTS

WO    WO-2004018634 A2    3/2004

OTHER PUBLICATIONS

Anand et al. (2002) "Structure of Oxalate Decarboxylase from *Bacillus subtilis* at 1.75 Å Resoltuion," Biochemistry, 41:7659-7669.
Campieri et al. (2001) "Reduction of oxaluria after an oral course of lactic acid bacteria at high concentration," Kidney International, 60:1097-1105.
Communication about intention to grant a European patent for European Application 07873799.6, dated Nov. 5, 2012 (5 pages).
Dashek et al. (1997) "Assay and Purification of Enzymes-Oxalate Decarboxylase," Methods in Plant Biochemistry and Molecular Biology, CRC Press, Chapter 5, pp. 49-71.
Earnest (1979) "Enteric Hyperoxaluria," Adv. Internal Medicine, 24:407-427.
Extended European Search Report for European Application 07873799.6, dated Mar. 12, 2010 (4 pages).
Gilliland (1988) "A Biological Macromolecule Crystallization Database: A Basis for a Crystallilzation Strategy," Journal of Crystal Growth, 90:51-59.
Grujic et al. (2009) "Hyperoxaluria is reduced and nephrocalcinosis prevented with an oxalate-degrading enzyme in mice with hyperoxaluria," American Journal of Nephrology, 29(2): 86-93.
Hochgrafe et al. (2007) "S-cysteinylation is a general mechanism for thiol protection of Bacillus subtilis proteins after oxidative stress," J Biol Chem, 282(36): 25981-5.

(Continued)

*Primary Examiner* — Suzanne M Noakes
(74) *Attorney, Agent, or Firm* — Goodwin Procter LLP

(57) ABSTRACT

Pharmaceutical compositions comprising spray-dried oxalate decarboxylase crystals are disclosed. Methods to treat a disorder associated with elevated oxalate concentration using compositions comprising spray-dried oxalate decarboxylase crystals are also disclosed.

15 Claims, 5 Drawing Sheets

Specification includes a Sequence Listing.

(56) References Cited

OTHER PUBLICATIONS

International Search Report and Written Opinion for International Patent Application No. PCT/US2007/075091, dated Aug. 6, 2008 (7 pages).

International Search Report and Written Opinion for International Patent Application No. PCT/US2014/012008, dated May 7, 2014 (19 pages).

Leumann et al. (1999) "What is new in primary hyperoxaluria?" Nephrol. Dial. Transplant., 14(11):2556-8.

Leumann et al. (2001) "The primary hyperoxalurias," J. Am. Soc. Nephrol., 12(9):1986-93.

Magro et al. (1988) "Enzymatic oxalate decarboxylation in isolates of *Sclerotinia sclerotiorum*," FEMS Microbiology Letters, 49:49-52.

Margolin (1996) "Novel Crystalline Catalysts," Trends Biotechnol., 14:223-30.

McPherson (1985) "Crystallization of macromolecules: general principles," Methods Enzymol., 114:112-20.

Monico et al. (2002) "Potential mechanisms of marked hyperoxaluria not due to primary hyperoxaluria I or II," Kidney Int., 62(2):392-400.

Office Action for Canadian Patent Application 2659081, dated Apr. 28, 2016 (7 pages).

Office Action for Canadian Patent Application 2659081, dated Dec. 9, 2013 (5 pages).

Office Action for Chinese Patent Application 201310106056.0, dated Aug. 19, 2016 (9 pages).

Office Action for Chinese Patent Application 201310106056.0, dated Jun. 14, 2017 (11 pages).

Office Action for Chinese Patent Application 201310106056.0, dated Mar. 5, 2014 (9 pages).

Parkinson et al. (1989) "The determination of plasma oxalate concentrations using an enzyme/bioluminescent assay. 2. Co-immobilisation of bioluminescent enzymes and studies of in vitro oxalogenesis," Clin. Chim. Acta., 179(1):97-108.

Svedruzic et al. (2005) "The enzymes of oxalate metabolism: unexpected structures and mechanisms," Arch. Biochem. Biophys., 433(1):176-92.

Tanner et al. (2000) "Bacillus subtilis YvrK is an acid-induced oxalate decarboxylase," J. Bacteriol., 182(18):5271-3.

Tanner et al. (2001) "Oxalate decarboxylase requires manganese and dioxygen for activity," J. Biol. Chem., 276(47):43627-34.

Vaghjiani et al. (2000) "Production and characterisation of cross-linked enzyme crystals (CLECs®) for application as process scale biocatalysts," Biocatalysis and Biotransformation, 18:151-175.

Zelinski et al. (1997) "Cross-Linked Enzyme Crystals (CLECs): Efficient and Stable Biocatalysts for Preparative Organic Chemistry," Angew. Chem. Int. Ed. Engl., 36(7):722-724.

\* cited by examiner

SEQUENCE LISTING

```
<160> NUMBER OF SEQ ID NOS: 1

<210> SEQ ID NO 1
<211> LENGTH: 385
<212> TYPE: PRT
<213> ORGANISM: Bacillus subtilis

<400> SEQUENCE: 1

Met Lys Lys Gln Asn Asp Ile Pro Gln Pro Ile Arg Gly Asp Lys Gly
1               5                   10                  15

Ala Thr Val Lys Ile Pro Arg Asn Ile Glu Arg Asp Arg Gln Asn Pro
            20                  25                  30

Asp Met Leu Val Pro Pro Glu Thr Asp His Gly Thr Val Ser Asn Met
        35                  40                  45

Lys Phe Ser Phe Ser Asp Thr His Asn Arg Leu Glu Lys Gly Gly Tyr
    50                  55                  60

Ala Arg Glu Val Thr Val Arg Glu Leu Pro Ile Ser Glu Asn Leu Ala
65                  70                  75                  80

Ser Val Asn Met Arg Leu Lys Pro Gly Ala Ile Arg Glu Leu His Trp
                85                  90                  95

His Lys Glu Ala Glu Trp Ala Tyr Met Ile Tyr Gly Ser Ala Arg Val
            100                 105                 110

Thr Ile Val Asp Glu Lys Gly Arg Ser Phe Ile Asp Asp Val Gly Glu
        115                 120                 125

Gly Asp Leu Trp Tyr Phe Pro Ser Gly Leu Pro His Ser Ile Gln Ala
    130                 135                 140

Leu Glu Glu Gly Ala Glu Phe Leu Leu Val Phe Asp Asp Gly Ser Phe
145                 150                 155                 160

Ser Glu Asn Ser Thr Phe Gln Leu Thr Asp Trp Leu Ala His Thr Pro
                165                 170                 175

Lys Glu Val Leu Ala Ala Asn Phe Gly Val Thr Lys Glu Glu Ile Ser
            180                 185                 190

Asn Leu Pro Gly Lys Glu Lys Tyr Ile Phe Glu Asn Gln Leu Pro Gly
        195                 200                 205

Ser Leu Lys Asp Asp Leu Val Glu Gly Pro Asn Gly Glu Val Pro Tyr
    210                 215                 220

Pro Phe Thr Tyr Arg Leu Leu Glu Gln Glu Pro Ile Glu Ser Glu Gly
225                 230                 235                 240

Gly Lys Val Tyr Ile Ala Asp Ser Thr Asn Phe Lys Val Ser Lys Thr
                245                 250                 255

Ile Ala Ser Ala Leu Val Thr Val Glu Pro Gly Ala Met Arg Glu Leu
            260                 265                 270
```

```
                            -continued

His Trp His Pro Asn Thr His Glu Trp Gln Tyr Tyr Ile Ser Gly Lys
        275                 280                 285

Ala Arg Met Thr Val Phe Ala Ser Asp Gly His Ala Arg Thr Phe Asn
    290                 295                 300

Tyr Gln Ala Gly Asp Val Gly Tyr Val Pro Phe Ala Met Gly His Tyr
305                 310                 315                 320

Val Glu Asn Ile Gly Asp Glu Pro Leu Val Phe Leu Glu Ile Phe Lys
                325                 330                 335

Asp Asp His Tyr Ala Asp Val Ser Leu Asn Gln Trp Leu Ala Met Leu
            340                 345                 350

Pro Glu Thr Phe Val Gln Ala His Leu Asp Leu Gly Lys Asp Phe Thr
        355                 360                 365

Asp Val Leu Ser Lys Glu Lys His Pro Val Val Lys Lys Lys Cys Ser
        370                 375                 380

Lys
385
```

CRYSTALLIZED OXALATE DECARBOXYLASE AND METHODS OF USE

CROSS-REFERENCE TO RELATED APPLICATIONS

This application is a continuation patent application under 35 U.S.C. § 120 of U.S. patent application Ser. No. 15/630,978, filed on Jun. 23, 2017 (now U.S. Pat. No. 10,246,755, issued on Apr. 2, 2019), which application is a continuation patent application under 35 U.S.C. § 120 of U.S. patent application Ser. No. 14/761,521, filed on Jul. 16, 2015 (now U.S. Pat. No. 9,714,456, issued on Jul. 25, 2017), which application is a U.S. national stage application under 35 U.S.C. § 371 of International Application No. PCT/US2014/012008, filed on Jan. 17, 2014, which claims the benefit of and priority to U.S. Provisional Patent Application No. 61/754,342, filed on Jan. 18, 2013, each of which is incorporated by reference herein in its entirety for all purposes.

Oxalic acid is a dicarboxylic acid of the formula $HO_2C$—$CO_2H$. Oxalic acid exists primarily as oxalate in biological organisms, which is the salt form of oxalic acid. Oxalate is found in foods, such as, e.g., spinach, rhubarb, strawberries, cranberries, nuts, cocoa, chocolate, peanut butter, sorghum, and tea. Oxalate is also a metabolic end product in humans and other mammals. It is excreted by the kidneys into the urine. When combined with calcium, oxalic acid produces an insoluble product, calcium oxalate, which is the most prevalent chemical compound found in kidney stones.

Because mammals do not synthesize enzymes that degrade oxalate, oxalate levels in an individual are normally held in check by excretion and low absorption of dietary oxalate. Elevated concentrations of oxalate are associated with a variety of pathologies, such as primary hyperoxaluria, enteric hyperoxaluria, and idiopathic hyperoxaluria. Leumann et al., *Nephrol. Dial, Transplant.* 11:2556-2558 (1999) and Earnest, *Adv. Internal Medicine* 24:407-427 (1979). Increased oxalate can be caused by consuming too much oxalate from foods, by hyperabsorption of oxalate from the intestinal tract, and by abnormalities of endogenous oxalate production. Hyperabsorption of oxalate in the colon and small intestine can be associated with intestinal diseases, including hyperabsorption caused by diseases of bile acid and fat malabsorption; Heal resection; and, for example, by steatorrhea due to celiac disease, exocrine pancreatic insufficiency, intestinal disease, and liver disease.

Hyperoxaluria, or increased urinary oxalate levels, is associated with a number of health problems related to the deposit of calcium oxalate in the kidney tissue (nephrocalcinosis) or urinary tract (e.g., kidney stones, urolithiasis, and nephrolithiasis), Calcium oxalate may also be deposited in, e.g., the eyes, blood vessels, joints, bones, muscles, heart and other major organs, causing damage to the same, See, e.g., Leumann et al. *J. Am. Soc. Nephrol.* 12:1986 1993 (2001) and Monica et al., *Kidney International* 62:392 400 (2002). The effects of increased oxalate levels can appear hi a variety of tissues. For example, deposits in small blood vessels cause painful skin ulcers that do not heal, deposits in bone marrow cause anemia, deposits in bone tissue cause fractures or affect growth in children, and calcium oxalate deposits in the heart cause abnormalities of heart rhythm or poor heart function.

Existing methods to treat elevated oxalate levels are not always effective and intensive dialysis and organ transplantation may be required in many patients with primary hyperoxaluria. Existing therapies for various hyperoxalurias include high-dose pyridoxine, orthophosphate, magnesium, iron, aluminum, potassium citrate, cholestyramine, and glycosaminoglycan treatment, as well as regimes for adjusting diet and fluid intake, for dialysis, and for surgical intervention, such as renal and liver transplantation. These therapies (e.g., low-oxalate or low-fat diet, pyridoxine, adequate calcium, and increased fluids), are only partially effective and they may have undesirable adverse side effects, such as the gastrointestinal effects of orthophosphate, magnesium, or cholestyramine supplementation d the risks of dialysis and surgery. Accordingly, methods that safely remove oxalate from the body are needed. Moreover, methods that degrade oxalate to reduce oxalate levels in a biological sample are advantageous over a therapy, for example, that solely blocks absorption or increases clearance of oxalate.

The present disclosure relates to pharmaceutical compositions of spray-dried oxalate decarboxylase ("OXDC") crystals and their uses to treat oxalate-associated disorders, e.g., hyperoxaluria. In some embodiments, pharmaceutical compositions comprising spray-dried crystalline oxalate decarboxylase can be administered to a mammal, e.g., orally or directly to the stomach, to reduce oxalate levels and/or to reduce damage caused by calcium oxalate deposits in the mammal.

The invention is based in part on the discovery that a crystalline form of oxalate decarboxylase can be spray-dried without destroying the protein crystals or their beneficial properties. It has previously been understood by those of skill in the art that protein crystals could not be spray-dried because the crystals would clog the spray-dryer during the manufacturing process. It was also believed that even if the spray-dryer could be adapted to process protein crystals, the crystals would be fractured and broken down to a dust during processing, essentially eliminating any advantages associated with the crystalline form. Thus, it is surprising and unexpected that pharmaceutical compositions of the invention comprise spray-dried oxalate decarboxylase crystals that retain their crystalline integrity, stability, and enzymatic activity, as well as providing the traditional advantages associated with spray-dried formulations.

The spray-dried oxalate decarboxylase crystal compositions of the present disclosure allow for increased activity per unit of weight or volume. For example, the compositions allow for increased density (i.e., increased weight per unit of volume), which enables one to fill more units of oxalate decarboxylase per unit of volume. In particular embodiments, spray-dried oxalate decarboxylase crystal compositions of the invention allow more units to be filled into a capsule of a given size. Accordingly, spray-dried oxalate decarboxylase crystal compositions of the present disclosure allow a therapeutically effective dose to be delivered orally, rather than by infusion or injection, and allow for a reduced pill burden. The spray-dried oxalate decarboxylase crystal compositions of the invention also improve stability, Without wishing to be bound by theory, it is believed that increased density contributes to improved stability. The spray-dried oxalate decarboxylase crystal compositions of the invention allow for manufacturing improvements, including improved stability and reduced waste from filling the spray-dried crystals directly into capsules as opposed to formulating with excipients, potentially reducing cost and decreasing production time.

The present disclosure further provides pharmaceutical compositions comprising spray-dried oxalate decarboxylase crystals that can deliver a higher level of activity into an oral dosage form of a given size. For example, in some embodiments, a size 000 capsule comprises at least 11,000 units (U), at least 22,000 U, at least 33,000 U, at least 44,000 U, at least 55,000 U, at least 66,000 U, or at least 77,000 U of spray-dried oxalate decarboxylase crystals (OXDC crystals). In some embodiments, a size 000 capsule comprises between 11,000 and 77,000 U of spray-dried OXDC crystals. In some embodiments, a size 000 capsule comprises between 22,000 and 77,000 U of OXDC crystals. In some embodiments, a size 000 capsule comprises between 33,000 and 77,000 U of spray-dried OXDC crystals. In some embodiments, a size 000 capsule comprises between 44,000 and 77,000 U of spray-dried OXDC crystals. In some embodiments, a size 000 capsule comprises between 55,000 and 77,000 U of spray-dried OXDC crystals. In some embodiments, a size 000 capsule comprises between 66,000 and 77,000 U of spray-dried OXDC crystals.

In some embodiments, a size 00 capsule comprises at least 8,000 U, at least 15,000 U, at least 23,000 U, at least 30,000 U, at least 38,000 U, at least 46,000 U, or at least 53,000 U of spray-dried OXDC crystals. In some embodiments, a size 00 capsule comprises between 8,000 and 53,000 U of spray-dried OXDC crystals. In some embodiments, a size 00 capsule comprises between 15,000 and 53,000 U of spray-dried OXDC crystals. In some embodiments, a size 00 capsule comprises between 23,000 and 53,000 U of spray-dried OXDC crystals. In some embodiments, a size 00 capsule comprises between 30,000 and 53,000 U of OXDC crystals. In some embodiments, a size 00 capsule comprises between 38,000 and 53,000 U of spray-dried OXDC crystals. In some embodiments, a size 00 capsule comprises between 46,000 and 53,000 U of spray-dried OXDC crystals.

In some embodiments, a size 0 capsule comprises at least 5,000 U, at least 11,000 U, at least 16,000 U, at least 22,000 U, at least 27,000 U, at least 33,000 U, or at least 38,000 U of OXDC crystals. In some embodiments, a size 0 capsule comprises between 5,000 and 38,000 U of spray-dried OXDC crystals. In some embodiments, a size 0 capsule comprises between 11,000 and 38,000 U of spray-dried OXDC crystals. In some embodiments, a size 0 capsule comprises between 16,000 and 38,000 U of OXDC crystals. In some embodiments, a size 0 capsule comprises between 22,000 and 38,000 U of spray-dried OXDC crystals. In some embodiments, a size 0 capsule comprises between 27,000 and 38,000 U of spray-dried OXDC crystals. In some embodiments, a size 0 capsule comprises between 33,000 and 38,000 U of spray-dried OXDC crystals.

In some embodiments, a size 1 capsule comprises at least 3,000 U, at least 6,000 U, at least 9,000 U, at least 12,000 U, at least 15,000 U, at least 18,000 U, or at least 21,000 U of spray-dried OXDC crystals. In some embodiments, a size 1 capsule comprises between 3,000 and 21,000 U of spray-dried OXDC crystals. In some embodiments, a size 1 capsule comprises between 6,000 and 21,000 U of spray-dried OXDC crystals. In some embodiments, a size 1 capsule comprises between 9,000 and 21,000 U of spray-dried OXDC crystals. In some embodiments, a size 1 capsule comprises between 12,000 and 21,000 U of spray-dried OXDC crystals. In some embodiments, a size 1 capsule comprises between 15,000 and 21,000 U of spray-dried OXDC crystals. In some embodiments, a size 1 capsule comprises between 18,000 and 21,000 U of spray-dried OXDC crystals.

In all cases a unit is defined as the amount of spray-dried oxalate decarboxylase crystals that will degrade one micromole of oxalate per minute at 37° C.

In a related aspect, the present disclosure features pharmaceutical compositions comprising spray-dried oxalate decarboxylase crystals which are substantially active and stable in variable pH conditions (e.g., about pH 2-9, about pH 2-7, or about pH 4-7), and/or in the presence of a protease, e.g., one or more of, e.g., pepsin, chymotrypsin, or pancreatin. In some embodiments, the pharmaceutical composition retains an activity at least 2-, 3-fold higher than the activity retained by a non-crystalline oxalate decarboxylase in acidic conditions (e.g., an acidic pH of about 2 to 3) and in the presence of a protease, as described herein. In other embodiments, the pharmaceutical composition is at least 200%, 300%, 400% more stable than a non-crystalline oxalate decarboxylase in acidic conditions (e.g., an acidic pH of about 2 to 3) and in the presence of a protease, as described herein. In some embodiments, the oxalate decarboxylase crystals are spray-dried cross-linked crystals. In some embodiments, the spray-dried oxalate decarboxylase crystals are not cross-linked.

In some embodiments, the spray-dried crystals include oxalate decarboxylase having a sequence identical or substantially identical to an oxalate decarboxylase sequence found in a natural source, such as a plant, bacterium and fungus, in particular from *Bacillus subtilis, Collybia velutipes* or *Flammulina velutipes, Aspergillus niger, Pseudomonas* sp. *Synechocystis* sp. *Streptococcus mutans, Trametes hirsute, Sclerotinia sclerotiorum, T. versicolor, Postia placenta, Myrothecium verrucaria, Agaricus bisporus, Methylobacteriurra extorquens, Pseudomonas oxalaticus, Ralstonia eutropha, Cupriavidus oxalaticus, Wautersia* sp., *Oxalicibacterium flavum, Ammoniiphilus oxalaticus, Vibrio oxalaticus, A. oxalativorans, Variovorax paradoxus, Xanthobacter autotrophicus, Aspergillus* sp., *Penicillium* sp., and *Mucor* species. In other embodiments, the oxalate decarboxylase is recombinantly produced.

In some embodiments, the cross-linked or uncross-linked crystals used in the compositions of the invention include oxalate decarboxylase having a sequence identical or substantially identical to the oxalate decarboxylase sequence from *Bacillus subtilis* (SEQ ID NO:1), In some embodiments, the oxalate decarboxylase comprises a modification of the cysteine residue at position 383 ("C383") of SEQ ID NO:1. In some embodiments, the modification comprises reaction of C383 with a thiol protecting group. In some embodiments, the oxalate decarboxylase comprises a sequence identical to SEQ ID NO:1, except that the cysteine residue at position 383 has been substituted with a different amino acid. In some embodiments, the oxalate decarboxylase comprises a sequence identical to SEQ ID NO:1, except that C383 has been deleted. In other embodiments, the oxalate decarboxylase comprises a sequence identical to SEQ ID NO:1, except that a C-terminal cysteine has been added to allow formation of an intramolecular disulfide ring. Because native or wild type oxalate decarboxylase may form a complex mixture of multimers, modification of C383 to reduce or eliminate the reactive thiol group can render the modified oxalate decarboxylase better suited for commercial scale of production. In one embodiment, protection of the C383 thiol group is carried out by cysteinylation.

In one aspect, the invention provides a method of reducing oxalate concentration in a subject by administering a pharmaceutical composition that comprises spray-dried cross-linked or uncross-linked oxalate decarboxylase crystals that are spray-dried as disclosed herein. In another aspect, the invention provides for use of any of the spray-dried cross-linked or uncross-linked oxalate decarboxylase crystal pharmaceutical compositions described herein in a method of reducing oxalate concentration in a subject. Administration of the pharmaceutical composition can cause a reduction of oxalate concentration by at least 10%, at least 20%, at least 30%, or at least 40% or more.

In some embodiments, the composition is administered orally or via an extracorporeal device. In one embodiment, the extracorporeal device is a catheter, e.g., a catheter coated with spray-dried oxalate decarboxylase crystals. In other embodiments, the composition is administered as a suspension, dry powder, capsule, or tablet. In one embodiment, the method of reducing oxalate concentration in a mammal includes a step of assaying the oxalate concentration in a biological sample of the mammal, such as a urine, blood, plasma, or serum sample.

In another aspect, the present disclosure provides a method of treating, preventing, and/or slowing the progression of a disorder associated with elevated oxalate concentrations in a mammal by administering pharmaceutical compositions comprising spray-dried cross-linked or uncross-linked oxalate decarboxylase crystals to the mammal. In one embodiment, the disorder associated with elevated oxalate concentration is a kidney disorder, joint disorder, eye disorder, liver disorder, gastrointestinal disorder, or pancreatic disorder. In certain embodiments, the disorder is primary hyperoxaluria, enteric hyperoxaluria, idiopathic hyperoxaluria, ethylene glycol poisoning, cystic fibrosis, inflammatory bowel disease, urolithiasis, nephrolithiasis, chronic kidney disease, hemodialysis, gastrointestinal bypass, and kidney stones.

The details of one or more embodiments of the present disclosure are set forth in the accompanying drawings and the description below.

DETAILED DESCRIPTION OF EMBODIMENTS

Figure 1:
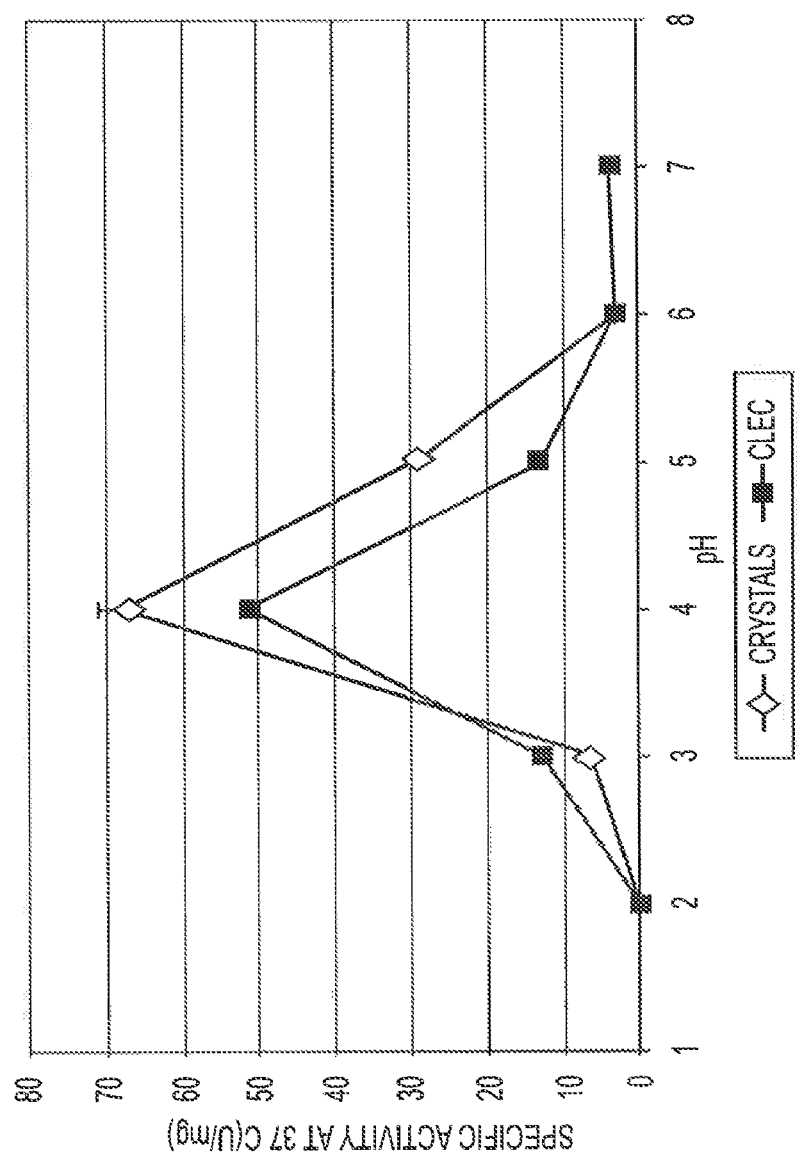
FIG. 1 is the pH activity profile of non cross-linked vs. cross-linked OXDC crystals (CLEC).

The present disclosure is based, in part, on the discovery that crystals of oxalate decarboxylase (OXDC) can be spray-dried for use in pharmaceutical compositions. These pharmaceutical compositions comprising spray-dried cross-linked or uncross-linked OXDC crystals and methods of administering them to treat the symptoms of hyperoxaluria and other oxalate-related disorders in a mammal are described herein.

Definitions

As used herein, a "biological sample" is biological material collected from cells, tissues, organs, or organisms, for example, to detect an analyte. Exemplary biological samples include a fluid, cell, or tissue sample. Biological fluids include, for example, serum, blood, plasma, saliva, urine, or sweat. Cell or tissue samples include biopsy, tissue, cell suspension, or other specimens and samples, such as clinical samples.

A "crystal" is one form of the solid state of matter, comprising atoms arranged in a pattern that repeats periodically in three dimensions (see, e.g., Barret, Structure of Metals, 2nd ed., McGraw-Hill, New York (1952)). A crystal form of a polypeptide, for example, is distinct from a second form—the amorphous solid state. Crystals display characteristic features including shape, lattice structure, percent solvent, and optical properties, such as, e.g., refractive index. An OXDC crystal may be cross-linked as described in U.S. Pat. No. 8,142,775, or uncrosslinked.

An "extracorporeal device" is a structure that is not within the body for bringing a body fluid in contact with spray-dried OXDC crystals in the treatment of an individual. Preferably, an extracorporeal device is a device used for dialysis, including kidney dialysis, a device for continuous arteriovenous hemofiltration, an extracorporeal membrane oxygenator, or other device used to filter waste products from the bloodstream. Similarly, components of devices to filter waste products are encompassed by the term, including a tube, a porous material, or a membrane, for example. In particular, an extracorporeal device may be a dialysis device. It may also be a membrane of a dialysis device.

A "functional fragment" of OXDC is a portion of an OXDC polypeptide that retains one or more biological activities of OXDC, such as the ability to catalyze the decarboxylation of oxalate. As used herein, a functional fragment may comprise terminal truncations from one or both termini, unless otherwise specified. For example, a functional fragment may have 1, 2, 4, 5, 6, 8, 10, 12, 15, or 20 or more residues omitted from the amino and/or carboxyl terminus of an OXDC polypeptide, Preferably, the truncations are not more than 20 amino acids from one or both termini, A functional fragment may optionally be linked to one or more heterologous sequences.

The term "individual" or "subject" refers to any mammal, including but not limited to, any animal classified as such, including humans, non human primates, primates, baboons, chimpanzees, monkeys, rodents (e.g., mice, rats), rabbits, cats, dogs, horses, cows, sheep, goats, pigs, etc.

The term "isolated" refers to a molecule that is substantially free of its natural environment. For instance, an isolated protein is substantially free of cellular material or other proteins from the cell or tissue source from which it is derived. The term refers to preparations where the isolated protein is sufficiently pure to be administered as a therapeutic composition, or at least 70% to 80% (w/w) pure, more preferably, at least 80% 90% (w/w) pure, even more preferably, 90 to 95% pure; and, most preferably, at least 95%, 96%, 97%, 98%, 99%, 99.5%, 99.8% or 100% (w/w) pure.

As used herein, the term "about" refers to up to ±10% of the value qualified by this term. For example, about 50 mM refers to 50 mM±5 mM; about 4% refers to 4%±0.4%.

As used herein, "oxalate-associated disorder" refers to a disease or disorder associated with pathologic levels of oxalic acid or oxalate, including, but not limited to hyperoxaluria, primarily hyperoxaluria, enteric hyperoxaluria, idiopathic hyperoxaluria, ethylene glycol (oxalate) poisoning, idiopathic urinary stone disease, renal failure 5 (including progressive, chronic, or end-stage renal failure), steatorrhoea, malabsorption, ileal disease, vulvodynia, cardiac conductance disorders, inflammatory bowel disease, cystic fibrosis, exocrine pancreatic insufficiency, Crohn's disease, ulcerative colitis, nephrocalcinosis, urolithiasis, and nephrolithiasis, Such conditions and disorders may optionally be acute or chronic. Oxalate-associated disorders associated with kidneys, bone, liver, gastrointestinal tract, and pancreas are known in the art. Further, it is well known that calcium oxalate can deposit in a wide variety of tissues including, but not limited to, the eyes, blood vessels, joints, bones, muscles, heart, and other major organs leading to a number of oxalate-associated disorders.

"Oxalic acid" exists predominantly in its salt form, oxalate (as salts of the corresponding conjugate base), at the pH of urine and intestinal fluid ($pK_{a1}$=1.23, $pK_{a2}$=4.19). Earnest, *Adv. Internal Medicine* 24:407 427 (1979). The terms "oxalic acid" and "oxalate" are used interchangeably throughout this disclosure. Oxalate salts comprising lithium, sodium, potassium, and iron (II) are soluble, but calcium oxalate is typically very poorly soluble in water (for example, dissolving only to about 0.58 mg/100 ml at 18° C. Earnest, *Adv. Internal Medicine* 24:407 427 (1979)). Oxalic acid from food is also referred to as dietary oxalate. Oxalate that is produced by metabolic processes is referred to as endogenous oxalate. Circulating oxalate is the oxalate present in a circulating body fluid, such as blood.

The terms "therapeutically effective dose," or "therapeutically effective amount," refer to that amount of a compound that results in prevention, delay of onset of symptoms, or amelioration of symptoms of an oxalate-related condition, including hyperoxaluria, such as primary hyperoxaluria or enteric hyperoxaluria. A therapeutically effective amount will, for example, be sufficient to treat, prevent, reduce the severity, delay the onset, and/or reduce the risk of occurrence of one or more symptoms of a disorder associated with elevated oxalate concentrations. The effective amount can be determined by methods well known in the art and as described in subsequent sections of this description.

The terms "treatment," "therapeutic method," and their cognates refer to treatment of an existing disorder and/or prophylactic/preventative measures. Those in need of treatment may include individuals already having a particular medical disorder, as well as those at risk or having, or who may ultimately acquire the disorder. The need for treatment is assessed, for example, by the presence of one or more risk factors associated with the development of a disorder, the presence or progression of a disorder, or likely receptiveness to treatment of a subject having the disorder. Treatment may include slowing or reversing the progression of a disorder.

Oxalate Decarboxylase

As used herein, oxalate decarboxylase (OXDC) (EC 4.1.1.2) refers to an oxalate carboxy-lyase enzyme. Oxalate decarboxylases are a group of enzymes known in the art to be capable of catalyzing the molecular oxygen ($O_2$) independent oxidation of oxalate to carbon dioxide and formate according to the following reaction:

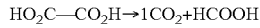

$HO_2C$—$CO_2H$→$1CO_2$+$HCOOH$

Isoforms of oxalate decarboxylase, and glycoforms of those isoforms, are included within this definition. OXDC from plants, bacteria and fungi are encompassed by the term, including the true oxalate decarboxylases from bacteria and fungi, such as *Bacillus subtilis, Collybia velutipes* or *Flammulina velutipes, Aspergillus niger, Pseudomonas* sp., *Synechocystis* sp., *Streptococcus mutans, Trametes hirsute, Sclerotinia sclerotiorum, T. versicolor, Postia placenta, Myrothecium verrucaria, Agaricus bisporus, Methylobacterium extorquens, Pseudomonas oxalaticus, Ralstonia eutropha, Cupriavidus oxalaticus, Wautersia* sp., *Oxalicibacterium flavum, Ammoniiphilus oxalaticus, Vibrio oxalaticus, A. oxalativorans, Variovorax paradoxus, Xanthobacter autotrophicus, Aspergillus* sp., *Penicillium* sp., and *Mucor* species. Optionally, the OXDC will be additionally dependent on coenzyme A, such as OXDC from organisms in the intestinal tract. In certain circumstances, OXDC is a soluble or insoluble hexameric protein.

Oxalate decarboxylases used to prepare the crystals, and which are used in methods described herein, may be isolated, for example, from a natural source, or may be derived from a natural source. As used herein, the term "derived from" means having an amino acid or nucleic acid sequence that naturally occurs in the source. For example, oxalate decarboxylase derived from *Bacillus subtilis* will comprise a primary sequence of a *Bacillus subtilis* oxalate decarboxylase protein, or will be encoded by a nucleic acid comprising a sequence found in *Bacillus subtilis* that encodes an oxalate decarboxylase or a degenerate thereof. A protein or nucleic acid derived from a source encompasses molecules that are isolated from the source, recombinantly produced, and/or chemically synthesized or modified. The crystals provided herein may be formed from polypeptides comprising amino acid sequences of OXDC or from a functional fragment of OXDC that retains oxalate degrading activity. Preferably, the OXDC retains at least one functional characteristic of a naturally occurring OXDC, e.g., the ability to catalyze degradation of oxalate, the ability to multimerize, and/or manganese requirement.

Isolated Oxalate Decarboxylase

Oxalate decarboxylases have been previously isolated and are thus available from many sources, including *Bacillus subtilis, Collybia velutipes* or *Flammulina velutipes, Aspergillus niger, Pseudomonas* sp., *Synechocystis* sp., *Streptococcus mutans, Trametes hirsute, Sclerotinia sclerotiorum, T. versicolor, Postia placenta, Myrothecium verrucaria, Agaricus bisporus, Methylobacterium oxtorqueris, Pseudomonas oxalaticus, Ralstonia eutropha, Cupriavidus oxalaticus, Wautersia* sp., *Oxalicibacterium flavum, Ammoniiphilus oxalaticus, Vibrio oxalaticus, A. oxalativorans, Variovorax paradoxus, Xanthobacter autotrophicus, Aspergillus* sp., *Penicillium* sp., and *Mucor* species. OXDC may also be purchased from commercial purveyors, such as, e.g., Sigma. Methods to isolate OXDC from a natural source are previously described, for example, in the following references: Tanner et al., *J. Biol. Chem.* 47:43627-43634 (2001); Dashek and Micales, *Methods in plant biochemistiy and molecular biology* Boca Raton, Fla.: CRC Press 5:49-71 (1997); Magro et al., *FEMS Microbiology Letters* 49: 49-52 (1988); Anand et al., *Biochemistry* 41:7659-7669 (2002); and Tanner and Bornemann, *J. Bacteriol.* 182: 5271-5273 (2000). These isolated oxalate decarboxylases may be used to form the crystals and methods described herein.

Recombinant Oxalate Decarboxylase

Alternatively, recombinant OXDCs may be used to form the crystals and methods provided herein. In some instances, recombinant OXDCs encompass or are encoded by sequences from a naturally occurring OXDC sequence. Further, OXDCs comprising an amino acid sequence that is homologous or substantially identical to a naturally occurring sequence are herein described. Also, OXDCs encoded by a nucleic acid that is homologous or substantially identical to a naturally occurring OXDC-encoding nucleic acid are provided and may be crystallized and/or administered as described herein.

Polypeptides referred to herein as "recombinant" are polypeptides which have been produced by recombinant DNA methodology, including those that are generated by procedures which rely upon a method of artificial recombination, such as the polymerase chain reaction (PCR) and/or cloning into a vector using restriction enzymes.

"Recombinant" polypeptides also include polypeptides having altered expression, such as a naturally occurring polypeptide with recombinantly modified expression in a cell, such as a host cell.

In one embodiment, OXDC is recombinantly produced from a nucleic acid that is homologous to a *Bacillus subtilis* or *Collybia velutipes* OXDC nucleic acid sequence, and sometimes it is modified, e.g., to increase or optimize recombinant production in a heterologous host. An example of such a modified sequence includes the nucleic acid sequence of the open reading frame of *Collybia velutipes* OXDC, for expression in *Candida boidinii*. The OXDC sequence may be modified to reduce its GC content, to be linked to a secretion signal sequence, e.g., an a Mating Factor secretion signal sequence, and/or to be flanked by engineered restriction endonuclease cleavage sites. In another embodiment, OXDC is recombinantly produced or from the unmodified *Bacillus subtilis* OXDC nucleic acid sequence which is available at GenBank Accession No:Z99120, The amino acid sequence encoded by this unmodified *Bacillus subtilis* OXDC nucleic acid sequence is provided as SEQ ID NO:1 as shown below.

Recombinant expression of OXDC is optionally controlled by a heterologous promoter, including a constitutive and/or inducible promoter, Promoters such as, e.g., T7, the alcohol oxidase (AOX) promoter, the dihydroxy-acetone synthase (DAS) promoters, the Gal 1,10 promoter, the phosphoglycerate kinase promoter, the glyceraldehyde-3-phosphate dehydrogenase promoter, alcohol dehydrogenase promoter, copper metallothionein (CUP1) promoter, acid phosphatase promoter, CMV and promoters polyhedrin are also appropriate. The particular promoter is selected based on the host or host cell. In addition, promoters that are inducible by methanol, copper sulfate, galactose, by low phosphate, by alcohol, e.g., ethanol, for example, may also be used and are well known in the art.

A nucleic acid that encodes OXDC may optionally comprise heterologous sequences. For example, a secretion sequence is included at the N-terminus of an OXDC polypeptide in some embodiments. Signal sequences such as

```
  1    MKKQNDIPQPIRGDKGATVKIPRNIERDRQNPDMLVPPETDHGTVSNMK

50    FSFSDTHNRLEKGGYAREVTVRELPISENLASVNMRLKPGAIRELHWHKE

100    AEWAYMIYGSARVTIVDEKGRSFIDDVGEGDLWYFPSGLPHSIQALEEGA

150    EFLLVFDDGSFSENSTFQLTDWLAHTPKEV1AANFGVTKEEISNLPGKEK

200    YIFENQLPGSLKDD1VEGPNGEVPYPETYRLLEQEPIESEGGKVYIADST

250    NFKVSKTIASALVTVEPGAMRELHWHPNTHEWQYYISGKARMTVFASDGH

300    ARTFNYQAGDVGYVPFAMGHYVENIGDEPLVFLEIFKDDHYADVSLNQWL

350    AMLPETFVQAHLDLGKDFTDVLSKEKHPVVKKKCSK              385
```

OXDC polypeptides useful for forming OXDC crystals may be expressed in a host cell, such as a host cell comprising a nucleic acid construct that includes a coding sequence for an OXDC polypeptide or a functional fragment thereof. A suitable host cell for expression of OXDC may be yeast, bacteria, fungus, insect, plant, or mammalian cell, for example, or transgenic plants, transgenic animals or a cell-free system. In some embodiments, a host cell is capable of glycosylating the OXDC polypeptide if necessary, capable of disulfide linkages, capable of secreting the OXDC, and/or capable of supporting multimerization of OXDC polypeptides. Preferred host cells include, but are not limited to *E. coli* (including *E. coli* Origami B and *E. coli* BL21), *Pichia pastoris, Saccharomyces cerevisiae, Schizosaccharomyces pombe, Bacillus subtilis, Aspergillus*, Sf9 cells, Chinese hamster ovary (CHO), 293 cells (human embryonic kidney), and other human cells. Also transgenic plants, transgenic animals including pig, cow, goat, horse, chicken, and rabbit are suitable hosts for production of OXDC.

For recombinant production of OXDC, a host or host cell may comprise a construct in the form of a plasmid, vector, phagemid, or transcription or expression cassette that comprises at least one nucleic acid encoding an OXDC or a functional fragment thereof. A variety of constructs are available, including constructs which are maintained in single copy or multiple copy, or which become integrated into the host cell chromosome. Many recombinant expression systems, components, and reagents for recombinant expression are commercially available, for example from Invitrogen Corporation (Carlsbad, Calif.); U.S. Biological (Swampscott, Mass.); BD Biosciences Pharmingen (San Diego, Calif.); Novagen (Madison, Wis.); Stratagene (La Jolla, Calif.); and Deutsche Sammlung von Mikroorganismen and Zellkulturen GmbH (DSMZ), (Braunschweig, Germany).

those from a Mating Factor, BGL2, yeast acid phosphatase (PHO), xylanase, alpha amylase, from other yeast secreted proteins, and secretion signal peptides derived from other species that are capable of directing secretion from the host cell may be useful. Similarly other heterologous sequences such as linkers (e.g., comprising a cleavage or restriction endonuclease site) and one or more expression control elements, an enhancer, a terminator, a leader sequence, and one or more translation signals are within the scope of this description. These sequences may optionally be included in a construct and/or linked to the nucleic acid that encodes OXDC. Unless otherwise specified, "linked" sequences can be directly or indirectly associated with one another.

Similarly, an epitope or affinity tag such as Histidine, HA (hemagglutinin peptide), maltose binding protein, AviTag®, FLAG, or glutathione-S-transferase may be optionally linked to the OXDC polypeptide. A tag may be optionally cleavable from the OXDC after it is produced or purified. A skilled artisan can readily select appropriate heterologous sequences, for example, match host cell, construct, promoter, and/or secretion signal sequence.

OXDC homologs or variants differ from an OXDC reference sequence by one or more residues. Structurally similar amino acids can be substituted for some of the specified amino acids, for example. Structurally similar amino acids include: (I, L and V); (F and Y); (K and R); (Q and N); (D and E); and (G and A). Deletion, addition, or substitution of amino acids is also encompassed by the OXDC homologs described herein. Such homologs and variants include (i) polymorphic variants and natural or artificial mutants, (ii) modified polypeptides in which one or more residues is modified, and (iii) mutants comprising one or more modified residues.

An OXDC polypeptide or nucleic acid is "homologous" (or is a "homolog") if it is at least 40%, 50%, 60%, 70%, 75%, 80%, 85%, 90%, 95%, 97%, 98%, 99%, or 100% identical to a reference sequence. If the homolog is not identical to the reference sequence, it is a "variant" A homolog is "substantially identical" to a reference OXDC sequence if the nucleotide or amino acid sequence of the homolog differs from the reference sequence (e.g., by truncation, deletion, substitution, or addition) by no more than 1, 2, 3, 4, 5, 8, 10, 20, or 50 residues, and retains (or encodes a polypeptide that retains) the ability to catalyze the degradation of oxalate. Fragments of an oxalate decarboxylase may be homologs, including variants and/or substantially identical sequences. By way of example, homologs may be derived from various sources of OXDC, or they may be derived from or related to a reference sequence by truncation, deletion, substitution, or addition mutation. Percent identity between two nucleotide or amino acid sequences may be determined by standard alignment algorithms such as, for example, Basic Local Alignment Tool (BLAST) described in Altschul et al., *J Mol. Biol.*, 215:403 410 (1990), the algorithm of Needleman et al., *J. Mol. Biol.*, 48:444 453 (1970), or the algorithm of Meyers et al., *Comput. Appl. Biosci.* 4:11-17 (1988). Such algorithms are incorporated into the BLASTN, BLASTP, and "BLAST 2 Sequences" programs (reviewed in McGinnis and Madden, *Nucleic Acids Res.* 32:W20-W25, (2004)). When utilizing such programs, the default parameters can be used. For example, for nucleotide sequences the following settings can be used for "BLAST 2 Sequences": program BLASTN, reward for match 2, penalty for mismatch 2, open gap and extension gap penalties 5 and 2 respectively, gap x_dropoff 50, expect 10, word size 11, filter ON, For amino acid sequences the following settings can be used for "BLAST 2 Sequences": program BLASTP, matrix BLOSUM62, open gap and extension gap penalties 11 and 1 respectively, gap x_dropoff50, expect 10, word size 3, filter ON. The amino acid and nucleic acid sequences for OXDCs that are appropriate to form the crystals described herein may include homologous, variant, or substantially identical sequences. In some embodiments, an OXDC homolog retains at least 40%, 50%, 60%, 70%, 75%, 80%, 85%, 90%, 95%, 97%, 98%, 99%, or 100% activity relative to a reference sequence.

Oxylate Decarboxylase Cysteine Modification

Without wishing to be bound by theory, thiol protection of C383 or elimination of the cysteine residue altogether, may enhance the formation of active oxalate decarboxylase hexamers, preventing oxidative dimerization among other oligomers. See, e.g., Tanner et al., *J. Biol. Chem.* 276(47): 43627-34 (2001). Thiol protection or elimination of the cysteine residue of oxalate decarboxylase allows the protein to be more readily processed into crystalline form for increased potency. To reduce problems that may impact commercial scale production of oxalate decarboxylase crystals, the C383 residue may be modified by substitution of the amino acid as described in U.S. Pat. No. 8,431,122 or by deletion of C383. Alternatively, the thiol group of C383 of the oxalate decarboxylase may be modified post-translationally with a thiol protecting group to prevent it from reacting with other groups. Thiol protecting groups are well-known to those skilled in the art and are described, for example, in Greene and Wuts, *Protecting Groups in Organic Synthesis*, Third Edition, Wiley, New York, (1999), and references cited therein. For example, the thiol group of C383 may be protected by converting it to a thioether, such as, e.g., an alkyl thioether, benzyl and substituted benzyl thioether, triphenylmethyl thioether, or silyl thioether; thioester; disulfide; thiocarbonate; or thiocarbamate. Alternatively, the thiol group of the C383 residue may be protected by adding a terminal cysteine, allowing the formation of an intramolecular disulfide bridge to prevent the cysteine from reacting with other molecules. In certain embodiments, the thiol group of C383 is protected by cysteinylation. The invention provides crosslinked and/or uncrosslinked crystals of oxalate decarboxylase modified by, for example, (1) elimination of C383, (2) addition of a C-terminal cysteine, or (3) reaction with a thiol protecting group by the invention (including cysteinylation) as well as compositions comprising spray-dried OXDC crystals bearing one of these modifications.

Purification of Oxalate Decarboxylase

Oxalate decarboxylase proteins or polypeptides may be purified from the source, such as a natural or recombinant source, prior to crystallization. A polypeptide that is referred to herein as "isolated" is a polypeptide that is substantially free of its natural environment, such as proteins, lipids, and/or nucleic acids of their source of origin (e.g., cells, tissue (i.e., plant tissue), or fluid or medium (in the case of a secreted polypeptide). Isolated polypeptides include those obtained by methods described herein or other suitable methods, and include polypeptides that are substantially pure or essentially pure, and polypeptides produced by chemical synthesis, by recombinant production, or by combinations of biological and chemical methods. Optionally, an isolated protein has undergone further processing after its production, such as by purification steps.

Purification may comprise buffer exchange and chromatographic steps, Optionally, a concentration step may be used, e.g., by dialysis, chromatofocusing chromatography, and/or associated with buffer exchange. In certain instances, cation or anion exchange chromatography is used for purification, including Q-sepharose, DEAF sepharose, DE52, sulfopropyl Sepharose chromatography or a CM52 or similar cation exchange column. Buffer exchange optionally precedes chromatographic separation, and may be performed by tangential flow filtration such as diafiltration. In certain preparations, OXDC is at least 70%, 80%, 85%, 90%, 95%, 96%, 97%, 98%, 99%, 99.5%, 99.7%, or 99.9% pure.

Purification in gram-scale runs is appropriate to prepare OXDC, and procedures are optimized for efficient, inexpensive, manufacturing-scale OXDC purification. For example, purification of at least 0.5, 1, 2, 5, 10, 20, 50, 100, 500, or 1000 grams or more of OXDC in a purification procedure is provided. In one exemplary procedure, tangential flow filtration of starting samples of at least 10 L, 50 L, 100 L, 500 L, WOOL or more is provided, allowing buffer exchange and precipitation of contaminant proteins. A single Q-sepharose column is optionally used for purification of OXDC.

Crystallization of Oxalate Decarboxylase

Oxalate decarboxylase crystals can be prepared using an OXDC polypeptide, such as a hexamer, as described above. See Anand et al., *Biochemistry* 41:7659-7669 (2002)). Vapor diffusion (such as, e.g., hanging drop and sitting drop methods), and batch methods of crystallization, for example, can be used. Oxalate decarboxylase crystals may be grown by controlled crystallization of the protein out of an aqueous solution or an aqueous solution that includes organic solvents. Conditions to be controlled include the rate of evaporation of solvent, the presence of appropriate co-solutes and buffers, pH, and temperature, for example.

For therapeutic administration, such as to treat a condition or disorder related to oxalate levels, a variety of OXDC crystal sizes are appropriate. In certain embodiments, crystals of less than about 500 μm average dimension are administered. Oxalate decarboxylase crystals with an average, maximal, or minimal dimension (for example) that is about 0.01, 0.1, 1, 5, 10, 25, 50, 100, 200, 300, 400, 500, or 1000 µm in length are also provided. Microcrystalline showers are also suitable.

Ranges are appropriate and would be apparent to the skilled artisan. For example, the protein crystals may have a longest dimension between about 0.01 µm and about 500 µm, alternatively, between 0.1 µm and about 50 µm. In a particular embodiment, the longest dimension ranges from about 0.1 µm to about 10 µm. Crystals may also have a shape chosen from spheres, needles, rods, plates, such as hexagons and squares, rhomboids, cubes, bipyramids and prisms. In illustrative embodiments, the crystals are cubes having a longest dimension of less than 5 µm.

In general, crystals are produced by combining the protein to be crystallized with an appropriate aqueous solvent or aqueous solvent containing appropriate crystallization agents, such as salts or organic solvents. The solvent is combined with the protein and optionally subjected to agitation at a temperature determined experimentally to be appropriate for the induction of crystallization and acceptable for the maintenance of protein activity and stability. The solvent can optionally include co-solutes, such as monovalent or divalent cations, co-factors or chaotropes, as well as buffer species to control pH. The need for co-solutes and their concentrations are determined experimentally to facilitate crystallization. In an industrial scale process, the controlled precipitation leading to crystallization can be carried out by the combination of protein, precipitant, co-solutes and, optionally, buffers in a batch process, for example. Alternative laboratory crystallization methods and conditions, such as dialysis or vapor diffusion, can be adopted (McPherson, et al., *Methods Enzymol.* 114:112-20 (1985) and Gilliland, *Crystal Growth* 90:51-59 (1998)). Occasionally, incompatibility between the cross-linking agent and the crystallization medium might require changing the buffers (solvent) prior to cross-linking.

As set forth in the Examples, oxalate decarboxylase crystallizes under a number of conditions, including a wide pH range (e.g., pH 3.5 to 8.0). A precipitant such as a polyethylene glycol (such as, e.g., PEG 200, PEG 400, PEG 600, PEG 1000, PEG 2000, PEG 3000, PEG 8000) or an organic cosolvent such as 2-methyl-2,4-pentanedial (MPD) is included in some embodiments as described. Common salts that may be used include sodium chloride, potassium chloride, ammonia sulfate, zinc acetate, etc.

Oxalate decarboxylase may be at a concentration of, e.g., at least 5, 10, 15, 20, 25, 30, 35, 40, 45, 50, 60, 70, 80, 90, or 100 mg/ml, or more in a crystallization broth. The efficiency or yield of a crystallization reaction is at least 50%, 60%, 70%, 80%, 90%, 91%, 92%, 93%, 94%, 95%, 96%, 97% 98%, 99%, or more. In one embodiment, crystals of oxalate decarboxylase are grown or produced by a batch process by mixing a solution of oxalate decarboxylase with an appropriate buffer.

Crystallization from Cells or Cell Extract

Crystals may be prepared directly from cells or crude cell extracts. In one embodiment, bacteria cells expressing oxalate decarboxylase are harvested. Cells are resuspended with or without DNase and homogenized. A salt solution is added to the cell lysis to reach a salt concentration of about 0.3 M, 0.4 M, 0.5 M, 0.6 M, up to 2.5 M, 3.0 M, 3.5 M, 4.0 M, or more. The salt added can be a sodium salt, a potassium salt, a calcium salt, or other salts, Proteins may be optionally extracted from the cell mixture by removing cell debris. In one embodiment, homogenized cell mixture is centrifuged, leaving proteins in the supernatant solution. Crystals are generated by reducing salt concentration of the cell mixture or protein solution. In one embodiment, salt is removed through dialysis to maintain protein concentration. To increase crystal yield, protein solution may be concentrated before salt concentration of the solution is reduced. Crystals may be generated at a solution with a pH of about 6, 7, 8 or 9.

Crystals may be prepared from a protein precipitate or pellet. In one embodiment, cells expressing desired proteins are harvested and oxalate decarboxylase protein is collected in a precipitate or pellet. Pellet or precipitate containing oxalate decarboxylase protein is solubilized in a salt solution. Crystals are formed by reducing salt concentration in the protein solution. For increased crystal yields, the salt concentration in the solubilized protein solution is at least about 0.3 M, 0.4 M, 0.5 M or more before it is reduced to produce crystals.

Crystals may also be prepared from a protein solution. In one embodiment, an oxalate decarboxylase protein solution is concentrated in a salt solution, and crystals are formed when the salt concentration in the solution is reduced. For increased crystal yields, the salt concentration is at least about 0.3 M, 0.4 M, 0.5 M or more before it is reduced to produce crystals.

Drying of Crystals of Oxalate Decarboxylase

Pharmaceutical proteins, including protein crystals may be dried in many ways, e.g., by removal of water, organic solvent or liquid polymer by means including drying with $N_2$, air or inert gases, vacuum oven drying, lyophilization, washing with a volatile organic solvent followed by evaporation of the solvent, evaporation in a fume hood, tray drying, fluid bed drying, spray drying, vacuum drying, or roller drying. Typically, tray drying, i.e. drying carried out by passing a stream of gas over wet crystals is used to pharmaceutical proteins. The gas may be selected from the group consisting of: nitrogen, argon, helium, carbon dioxide, air or combinations thereof. Drying is achieved when the crystals become a free flowing powder.

Spray drying is rarely used to prepare pharmaceutical grade proteins due to concerns related to sterility. No reports of spray-dried crystals have been found in the literature. Prior to this invention, it was widely believed that protein crystals could not be spray-dried because the crystals would clog the spray-dryer during the manufacturing process and that even if the spray-dryer could be adapted to process protein crystals, the crystals themselves would not survive the process. It was expected that the crystals would be fractured and broken down to a dust during processing, essentially eliminating any advantages associated with the crystalline form. Thus, it is surprising and unexpected that pharmaceutical compositions of the invention comprise spray-dried oxalate decarboxylase crystals that retain their crystalline integrity, stability, and enzymatic activity, as well as providing advantages associated with spray-dried formulations.

Spray drying oxalate decarboxylase crystals allows water to be separated from the crystal preparation, allowing for continuous production of dry solids in powder, granulate, or agglomerate form from liquid feedstocks such as emulsions and pumpable suspensions. Solutions of crystals cannot be used because once the crystals are dissolved, the crystals do not reform upon drying.

Spray drying involves the atomization of a liquid feedstock comprising OXDC crystals into a spray of droplets and contacting the droplets with hot air or gas in a drying chamber. The atomization process is best conducted using a two-fluid atomizer that mixes the liquid feedstock with a drying gas such as compressed air or nitrogen. One-fluid and rotary atomizers develop high-shear which could easily break the crystals. Evaporation of moisture from the droplets and formation of dry particles proceed under controlled temperature and airflow conditions.

Because of an evaporative cooling effect during the critical drying period and because the time of exposure to high temperatures of the dry material is generally short, the process results in little damage to the crystalline protein. Dried crystalline protein powder is discharged continuously from the drying chamber. Operating conditions and dryer design are selected according to the drying characteristics of the OXDC crystals and the desired powder qualities. The dried OXDC crystals are then tested for compliance with quality standards regarding particle size distribution, residual moisture content, bulk density and particle shape. In some embodiments excipients or ingredients selected from sugars, sugar alcohols, viscosity increasing agents, wetting or solubilizing agents, buffer salts, emulsifying agents, antimicrobial agents, antioxidants, water soluble polymers, amino acids and coating agents are added directly to the liquid feedstocks prior to spray drying. The excipient concentration is typically between about 10% and about 50% (w/w). The crystal concentration is typically between about 5% and about 25% (w/w). Crystal suspensions with and without excipients can be frozen at about −10° C. to about −70° C. for up to one year without a detrimental impact on the crystal structure or activity.

Compositions Comprising Spray-Dried OXDC Crystals

Spray-dried OXDC crystals are provided as a composition, such as a pharmaceutical composition (see, e.g., U.S. Pat. No. 6,541,606, describing formulations and compositions of protein crystals). Pharmaceutical compositions comprising spray-dried OXDC crystals may include one or more ingredients or excipients, including, but not limited to sugars and biocompatible polymers. Examples of excipients are described in Handbook of Pharmaceutical Excipients, published jointly by the American Pharmaceutical Association and the Pharmaceutical Society of Great Britain, and further examples are set forth below.

The OXDC enzyme may be administered as a spray-dried crystal in a composition as any of a variety of physiologically acceptable salt forms, and/or with an acceptable pharmaceutical carrier and/or additive as part of a pharmaceutical composition.

Physiologically acceptable salt forms and standard pharmaceutical formulation techniques and excipients are well known to persons skilled in the art (see, e.g., Physician's Desk Reference (PDR) 2003, 57th ed., Medical Economics Company, 2002; and Remington: The Science and Practice of Pharmacy, eds. Gennado et al., 20th ed, Lippincott, Williams & Wilkins, 2000). For the purposes of this application, "formulations" include "crystal formulations."

Oxalate decarboxylase useful in the methods of the present disclosure may be combined with an excipient. According to the present disclosure, an "excipient" acts as a filler or a combination of fillers used in pharmaceutical compositions. Exemplary ingredients and excipients for use in the compositions are set forth as follows.

Sugars

The sugar used as an excipient may be a monosaccharide, disaccharide, oligosaccharide, or polysaccharide. Exemplary monosaccharides include but are not limited to ribose, arabinose, xylose, lyxose, allose, altrose, glucose, mannose, gulose, fructose, iodose, galactose, xylitol, sucralose and talose, Exemplary disaccharides include but are not limited to sucrose, lactose, maltose, lactulose, trehalose, and cellobiose.

Biocompatible Polymers

Biocompatible polymers are polymers that are non-antigenic, non-carcinogenic, non-toxic and which are not otherwise inherently incompatible with living organisms may be used in the OXDC crystal compositions described herein. Examples include: poly (acrylic acid), poly (cyanoacrylates), poly (amino acids), poly (anhydrides), poly (depsipeptide), poly (esters) such as poly (lactic acid) or PLA, poly (lactic-co-glycolic acid) or PLGA, poly (β-hydroxybutyrate), poly (caprolactone) and poly (dioxanone); poly (ethylene glycol), poly ((hydroxypropyl)methacrylamide, poly [(organo)phosphazene], poly (ortho esters), poly (vinyl alcohol), poly (vinylpyrrolidone), maleic anhydride-alkyl vinyl ether copolymers, pluronic polyols, albumin, alginate, cellulose and cellulose derivatives, collagen, fibrin, gelatin, hyaluronic acid, oligosaccharides, glycaminoglycans, sulfated polysaccharides, blends and copolymers thereof.

Biodegradable Polymers

Biodegradable polymers degrade by hydrolysis or solubilization may be included in OXDC crystal compositions, Degradation can be heterogenous (occurring primarily at the particle surface), or homogenous (degrading evenly throughout the polymer matrix). Ingredients such as one or more excipients or pharmaceutical ingredients or excipients may be included in OXDC crystal compositions. An ingredient may be an inert or active ingredient.

In some embodiments, the pharmaceutical composition comprises crystallized oxalate decarboxylase which is spray-dried. In other embodiments, an excipient is added to the crystallized oxalate decarboxylase, and then the mixture is spray-dried to form the pharmaceutical composition. In certain embodiments, the excipient is a sugar. In certain embodiments, the sugar is a monosaccharide or a disaccharide. In some embodiments the excipient is trehalose, sucrose, or glucose. In certain embodiments the excipient is trehalose.

In an exemplary embodiment, trehalose is added to oxalate decarboxylase crystals and the mixture is spray-dried to form a pharmaceutical composition.

Flow Characteristics of Spray-Dried OXDC Crystals

According to the USP, the generally accepted scale of flowability is given in

TABLE 1

Table 1. Scale of Flowability

| Flow Character | Hausner Ratio |
|---|---|
| Excellent | 1.00-1.11 |
| Good | 1.12-1.18 |
| Fair | 119-1.25 |
| Passable | 1.26-1.34 |
| Poor | 1.35-1.45 |
| Very Poor | 1.46-1.59 |
| Very, very poor | >1.60 |

In some embodiments, the flowability of the pharmaceutical composition is "passable" or better per USP, i.e., the Hausner ratio is 1.34 or less. In some embodiments, the flowability of the pharmaceutical composition is "fair" or better per USP, i.e., the Hausner ratio is 1.25 or less. In further embodiments, the flowability of the pharmaceutical composition is "good" or better per USP, i.e., the Hausner ratio is 1.18 or less. In some embodiments the Hausner ratio of the pharmaceutical composition is from about 1.12 to about 1.18.

In some embodiments the pharmaceutical composition exhibits better stability than non-crystalline oxalate decarboxylase at a pH from about 3.5 to about 8 or 9. In some embodiments the pharmaceutical composition exhibits better stability than non-crystalline oxalate decarboxylase at a pH from about 3.5 to about 7. In some embodiments the pharmaceutical composition exhibits better stability than non-crystalline oxalate decarboxylase at a pH from about 3.5 to about 6. In some embodiments the pharmaceutical composition exhibits better stability than non-crystalline oxalate decarboxylase at a pH from about 3.5 to about 5. In some embodiments, the pharmaceutical composition exhibits better stability than soluble oxalate decarboxylase at a pH of about 3.7. In some embodiments the pharmaceutical composition exhibits better stability than non-crystalline oxalate decarboxylase in the presence of pepsin, trypsin or chymotrypsin.

In some embodiments the pharmaceutical composition is filled into capsules. In some embodiments the gelatin capsules are size 000, 00, 0, 1 or 2 capsules. In some embodiments the pharmaceutical composition is pressed into tablets. In some embodiments the pharmaceutical composition is blended to form a suspension. In some embodiments the capsules, tablets, or suspension comprising the pharmaceutical composition are suitable for oral administration.

Methods of Treating Oxalate-Associated Disorders with Spray-Dried OXDC Crystals

The methods of the present disclosure comprise administering an oxalate decarboxylase, e.g., spray-dried crystals of OXDC, or cross-linked forms thereof, to a mammalian subject to treat, prevent, or reduce the risk of occurrence of a condition associated with elevated levels of oxalate. The elevated levels of oxalate may be detected, e.g., in a biological sample from the subject, such as a body fluid, including urine, blood, serum, or plasma. In certain embodiments, urinary oxalate levels are detected. The crystals and/or the compositions comprising crystals may be administered in the methods described herein.

In some embodiments, methods are provided for treating hyperoxaluria in individuals with primary hyperoxaluria, enteric hyperoxaluria, hyperoxaluria caused by surgical intervention, idiopathic hyperoxaluria, oxalosis are provided. In other instances, elevated oxalate-related disorders of the kidneys, bone, liver gastrointestinal tract and pancreas are amenable to treatment with the methods disclosed herein. Further disorders or diseases treated by the methods provided herein include, but are not limited to ethylene glycol (oxalate) poisoning, idiopathic urinary stone disease, renal failure (including progressive, chronic, or end-stage renal failure), steatorrhoea, malabsorption, ileal disease, vulvodynia, cardiac conductance disorders, inflammatory bowel disease, cystic fibrosis, exocrine pancreatic insufficiency, Crohn's disease, ulcerative colitis, nephrocalcinosis, osteoporosis, urolithiasis, and nephrolithiasis. Such conditions and disorders may optionally be acute or chronic.

The methods of the present disclosure may reduce oxalate levels in a subject by at least 10%, 20%, 30%, 40%, 50%, 60%, 70%, 80%, 90%, 95%, or more as compared to levels in an untreated or control subject. In some embodiments, reduction is measured by comparing the oxalate level in a subject before and after administration of OXDC. In some embodiments, the present disclosure provides a method of treating or ameliorating an oxalate-associated condition or disorder, to allow one or more symptoms of the condition or disorder to improve by at least 10%, 20%, 30%, 40%, 50%, 60%, 70%, 80%, 90%, 95% or more. In certain embodiments the methods reduce levels of endogenous oxalate and/or adsorption of dietary oxalate.

In some embodiments, methods for treating individuals having a genotype associated with high oxalate levels are provided, such as individuals homozygous or heterozygous for a mutation that reduces activity of, e.g., alanine:glyoxalate aminotransferase, glyoxylate reductase/hydroxypyruvate reductase, hepatic glycolate oxidase, or another enzyme involved in oxalate metabolism or associated with hyperoxaluria. In other embodiments, methods for treating individuals having reduced or lacking *Oxalobacter formigenes* enteric colonization are provided.

The disclosed methods include administering therapeutically effective amounts of oxalate decarboxylase to a mammalian subject at risk for, susceptible to, or afflicted with a condition associated with elevated levels of oxalate. The populations treated by the methods of the present disclosure include, but are not limited to, subjects suffering from, or at risk for developing an oxalate-associated disorder such as, e.g., primary hyperoxaluria or enteric hyperoxaluria.

Subjects treated according to the methods of the present disclosure include but are not limited to mammals, including humans, non human primates, primates, baboons, chimpanzees, monkeys, rodents (e.g., mice, rats), rabbits, cats, dogs, horses, cows, sheep, goats, pigs, etc.

Indication, Symptoms, and Disease Indicators

Many methods are available to assess development or progression of an oxalate-associated disorder or a condition associated with elevated oxalate levels. Such disorders include, but are not limited to, any condition, disease, or disorder as defined above. Development or progression of an oxalate-associated disorder may be assessed by measurement of urinary oxalate, plasma oxalate, measurement of kidney or liver function, or detection of calcium oxalate deposits, for example.

A condition, disease, or disorder may be identified by detecting or measuring oxalate concentrations, for example, in a urine sample or other biological sample or fluid. An early symptom of hyperoxaluria is typically kidney stones, which may be associated with severe or sudden abdominal or flank pain, blood in the urine, frequent urges to urinate, pain when urinating, or fever and chills. Kidney stones may be symptomatic or asymptomatic, and may be visualized, for example by imaging the abdomen by x-ray, ultrasound, or computerized tomography (CT) scan. If hyperoxaluria is not controlled, the kidneys are damaged and kidney function is impaired. Kidneys may even fail.

Kidney failure (and poor kidney function) may be identified by a decrease in, or lacking urine output (glomerular filtration rate), general ill feeling, tiredness, and marked fatigue, nausea, vomiting, anemia, and/or failure to develop and grow normally in young children.

Calcium oxalate deposits in other tissues and organs may also be detected by methods including direct visualization (e.g. in the eyes), x-ray, ultrasound, CT, echocardiogram, or biopsy (e.g., bone, liver, or kidney). Kidney and liver function, as well as oxalate concentrations, may also be assessed using art-recognized direct and indirect assays. The chemical content of urine, blood or other biological sample may also be tested by well known techniques. For example, oxalate, glycolate, and glycerate levels may be measured. Assays for liver and kidney function are well known, such as, for example, the analysis of liver tissue for enzyme deficiencies and the analysis of kidney tissue for oxalate deposits. Samples may also be tested for DNA changes known to cause primary hyperoxaluria.

Other indications for treatment include, but are not limited to, the presence of one or more risk factors, including those discussed previously and in the following sections. A subject at risk for developing or susceptible to a condition, disease, or disorder or a subject who may be particularly receptive to treatment with oxalate decarboxylase may be identified by ascertaining the presence or absence of one or more such risk factors, diagnostic, or prognostic indicators. Similarly, an individual at risk for developing an oxalate-related disorder may be identified by analysis of one or more genetic or phenotypic markers.

The methods disclosed are useful in subjects with urinary oxalate levels of at least 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, or 400 mg of oxalate per 24 hour period, or more. In certain embodiments, the oxalate level is associated with one or more symptoms or pathologies. Oxalate levels may be measured in a biological sample, such as a body fluid including blood, serum, plasma, or urine. Optionally, oxalate is normalized to a standard protein or substance, such as creatinine in urine. In some embodiments, the claimed methods include administration of oxalate decarboxylase to reduce circulating oxalate levels in a subject to undetectable levels, or to less than 1%, 2%, 5%, 10%, 20%, 30%, 40%, 50%, 60%, 70%, or 80% of the subject's oxalate levels prior to treatment, within 1, 3, 5, 7, 9, 12, or 15 days.

Hyperoxaluria in humans can be characterized by urinary oxalate excretion of greater than 40 mg (approximately 440 µmol) or 30 mg per day. Exemplary clinical cutoff levels are 43 mg/day (approximately 475 µmol) for men and 32 mg/day (approximately 350 µmol) for women, for example. Hyperoxaluria can also be defined as urinary oxalate excretion greater than 30 mg per day per gram of urinary creatinine. Persons with mild hyperoxaluria may excrete at least 30-60 (342-684 µmol) or 40-60 (456-684 µmol) mg of oxalate per day. Persons with enteric hyperoxaluria may excrete at least 80 mg of urinary oxalate per day (912 µmol), and persons with primary hyperoxaluria may excrete at least 200 mg per day (2280 µmol).

Administration of Spray-Dried OXDC Crystals and Compositions

Administration of oxalate decarboxylase in accordance with the methods of the present disclosure is not limited to any particular delivery system and includes administration via the upper gastointestinal tract, e.g., the mouth (for example in capsules, liquid suspension, tablets, or with food), or the stomach, or upper intestine (for example by tube or injection) to reduce oxalate levels in an individual. In certain cases, the OXDC is administered to reduce endogenous oxalate levels and/or concentrations, OXDC may also be provided by an extracorporeal device, such as a dialysis apparatus, a catheter, or a structure or device that contacts a biological sample from an individual.

Administration to an individual may occur in a single dose or in repeat administrations, and in any of a variety of physiologically acceptable forms, and/or with an acceptable pharmaceutical carrier and/or additive as part of a pharmaceutical composition (described earlier). In the disclosed methods, oxalate decarboxylase may be administered alone, concurrently or consecutively over overlapping or nonoverlapping intervals with one or more additional biologically active agents, such as, e.g., pyridoxine (vitamin B-6), orthophosphate, magnesium, glycosaminoglycans, calcium, iron, aluminum, magnesium, potassium citrate, cholestyramine, organic marine hydrocolloid, plant juice, such as, e.g., banana stem juice or beet juice, or L-cysteine. Biologically active agents that reduce oxalate levels or that increase the activity or availability of OXDC are provided. In sequential administration, the oxalate decarboxylase and the additional agent or agents may be administered in any order. In some embodiments, the length of an overlapping interval may be more than 2, 4, 6, 12, 24, or 48 weeks or more.

The oxalate decarboxylase may be administered as the sole active compound or in combination with another active compound or composition. Unless otherwise indicated, the oxalate decarboxylase is administered as a dose of approximately from 10 µg/kg to 25 mg/kg or 100 mg/kg, depending on the severity of the symptoms and the progression of the disease. The appropriate therapeutically effective dose of OXDC is selected by a treating clinician and would range approximately from 10 µg/kg to 20 mg/kg, from 10 µg/kg to 10 mg/kg, from 10 µg/kg to 1 mg/kg, from 10 µg/kg to 100 µg/kg, from 100 µg/kg to 1 mg/kg, from 100 µg/kg to 10 mg/kg, from 500 µg/kg to 5 mg/kg, from 500 µg/kg to 20 mg/kg, from 1 mg/kg to 5 mg/kg, from 1 mg/kg to 25 mg/kg, from 5 mg/kg to 100 mg/kg, from mg/kg to 50 mg/kg, from 5 mg/kg to 25 mg/kg, and from 10 mg/kg to 25 mg/kg. Additionally, specific dosages indicated in the Examples or in the Physician's Desk Reference (PDR) 2003, 57th ed., Medical Economics Company, 2002, may be used.

In some embodiments the dosage of oxalate decarboxylase is about 900, about 3600, about 10800, or about 18000 units oxalate decarboxylase. In some embodiments the dosage is about 1500 units oxalate decarboxylase per capsule. In some embodiments the dosage of oxalate decarboxylase is about 112, about 450, about 1350, or about 2250 mg oxalate decarboxylase. In some embodiments the dosage is about 190 mg oxalate decarboxylase per capsule. In some embodiments, 1, 2, 3, 4, 5, 6, 7, 8, 9, 10, 11, 12, 13, 14, or 15 capsules are administered to a mammal, such as a human, per day. In some embodiments the capsules are administered with food, such as a snack or meal.

The oxalate decarboxylase crystal of the present disclosure may be administered through an extracorporeal device or catheter, such as for delivery of oxalate decarboxylase to a patient. Catheters, for example, urinary catheters, may be coated with compositions containing oxalate decarboxylase crystals.

In some embodiments, the oxalate decarboxylase crystals retain at least 50%, 60%, 70%, 80%, 90%, 95%, or 99% of their activity after 120 minutes at pH 9. In some embodiments, the oxalate decarboxylase crystals retain at least 50%, 60%, 70%, 80%, 90%, 95%, or 99% of their activity after 120 minutes at pH 8. In some embodiments, the oxalate decarboxylase crystals retain at least 50%, 60%, 70%, 80%, 90%, 95%, or 99% of their activity after 120 minutes at pH 7. In some embodiments, the oxalate decarboxylase crystals retain at least 50%, 60%, 70%, 80%, 90%, 95%, or 99% of their activity after 120 minutes at pH 6. In some embodiments, the oxalate decarboxylase crystals retain at least 50%, 60%, 70%, 80%, 90%, 95%, or 99% of their activity after 120 minutes at pH 5. In some embodiments, the oxalate decarboxylase crystals retain at least 50%, 60%, 70%, 80%, 90%, 95%, or 99% of their activity after 120 minutes at pH 4. In some embodiments, the oxalate decarboxylase crystals retain at least 50%, 60%, 70%, 80%, 90%, 95%, or 99% of their activity after 60 minutes at pH 7. In some embodiments, the oxalate decarboxylase crystals retain at least 50%, 60%, 70%, 80%. 90%, 95%, or 99% of their activity after 60 minutes at pH 6. In some embodiments, the oxalate decarboxylase crystals retain at least 50%, 60%, 70%, 80%, 90%, 95%, or 99% of their activity after 60 minutes at pH 5. In some embodiments, the oxalate decarboxylase crystals retain at least 50%, 60%, 70%, 80%, 90%, 95%, or 99% of their activity after 60 minutes at pH 4. In some embodiments, the oxalate decarboxylase crystals retain at least 50%, 60%, 70%, 80%, 90%, 9, or 99% of their activity after 30 minutes at pH 7. In some embodiments, the oxalate decarboxylase crystals retain at least 50%, 60%, 70%, 80%, 90%, 95%, or 99% of their activity after 30 minutes at pH 6. In some embodiments, the oxalate decarboxylase crystals retain at least 50%, 60%, 70%, 80%, 90%, 95%, or 99% of their activity after 30 minutes at pH 5. In some embodiments, the oxalate decarboxylase crystals retain at least 50%, 60%, 70%, 80%, 90%, 95%, or 99% of their activity after 30 minutes at pH 4.

In some embodiments, the oxalate decarboxylase crystals retain at least 50%, 60%, 70%, 80%, 90%, 95%, or 99% of their activity after 120 minutes in simulated gastric fluid (SGF; pH 3.7) with pepsin. In some embodiments, the oxalate decarboxylase crystals retain at least 50%, 60%, 70%, 80%, 90%, 95%, or 99% of their activity after 60 minutes in simulated gastric fluid (SGF; pH 3.7) with pepsin. In some embodiments, the oxalate decarboxylase crystals retain at least 50%, 60%, 70%, 80%, 90%, 95%, or 99% of their activity after 30 minutes in simulated gastric fluid (SGF; pH 3.7) with pepsin.

In some embodiments the spray-dried crystals retain at least 50%, 60%, 70%, or 80%, of their activity after 3 weeks at 40° C. and 75% RH. In some embodiments the spray-dried crystals retain at least 50%, 60%, 70%, 80%, or 85% of their activity after 2 weeks at 40° C. and 75% RH. In some embodiments the spray-dried crystals retain at least 50%, 60%. 70%. 80%, or 90% of their activity after 1 week at 40° C. and 75% RH.

In some embodiments the spray-dried crystals with trehalose retain at least 50%, 60%, 70%, 80%, 90%, or 100% of their activity after 3 weeks. In some embodiments the spray-dried crystals with trehalose retain at least 50%, 60%, 70%, 80%, 90%, or 100% of their activity after 2 weeks. In some embodiments the spray-dried crystals with trehalose retain at least 50%, 60%, 70%, 80%, 90%, or 100% of their activity after 1 week. In some embodiments the spray-dried crystals with sucrose retain at least 50%, 60%, 70%, 80%, 90%, or 100% of their activity after 3 weeks. In some embodiments the spray-dried crystals with sucrose retain at least 50%, 60%, 70%, 80%, 90%, or 100% of their activity after 2 weeks. In some embodiments the spray-dried crystals with sucrose retain at least 50%, 60%, 70%, 80%, 90%, or 100% of their activity after 1 week. In some embodiments the spray-dried crystals with Kolloidon VA64 retain at least 50%, 60%, 70%, 80%, 90%, or 100% of their activity after 3 weeks. In some embodiments the spray-dried crystals with Kolloidon VA64 retain at least 50%, 60%, 70%, 80%, 90%, or 100% of their activity after 2 weeks. In some embodiments the spray-dried crystals with Kolloidon VA64 retain at least 50%, 60%, 70%, 80%, 90%, or 100% of their activity after 1 week. In some embodiments the spray-dried crystals with Kolloidon 12PF retain at least 50%, 60%, 70%, 80%, 90%, or 100% of their activity after 3 weeks. In some embodiments the spray-dried crystals with Kolloidon 12PF retain at least 50%, 60%, 70%, 80%, 90%, or 100% of their activity after 2 weeks. In some embodiments the spray-dried crystals with Kolloidon 12PF retain at least 50%, 60%, 70%, 80%, 90%, or 100% of their activity after 1 week.

The following examples provide illustrative embodiments of the present disclosure. One of ordinary skill in the art will recognize the numerous modifications and variations that may be performed without altering the spirit or scope of the present disclosure. Such modifications and variations are encompassed within the scope of the present disclosure. The Examples do not in any way limit the present disclosure.

EXAMPLES

Oxalate decarboxylase crystals are designed to be active in the stomach and will be administered in the fed-state at a stomach pH >4. The following in vitro studies demonstrated that the cross-linked and non-cross-linked OXDC were comparable relative to activity and stability.

Example 1

OXDC specific activity at 37° C. as a function of pH is shown in FIG. 1. These results demonstrate that non-cross-linked OXDC (crystals) has the same or higher specific activity than the crosslinked material (OXDC CLEC) over the pH ranges evaluated.

Example 2

Figure 2:
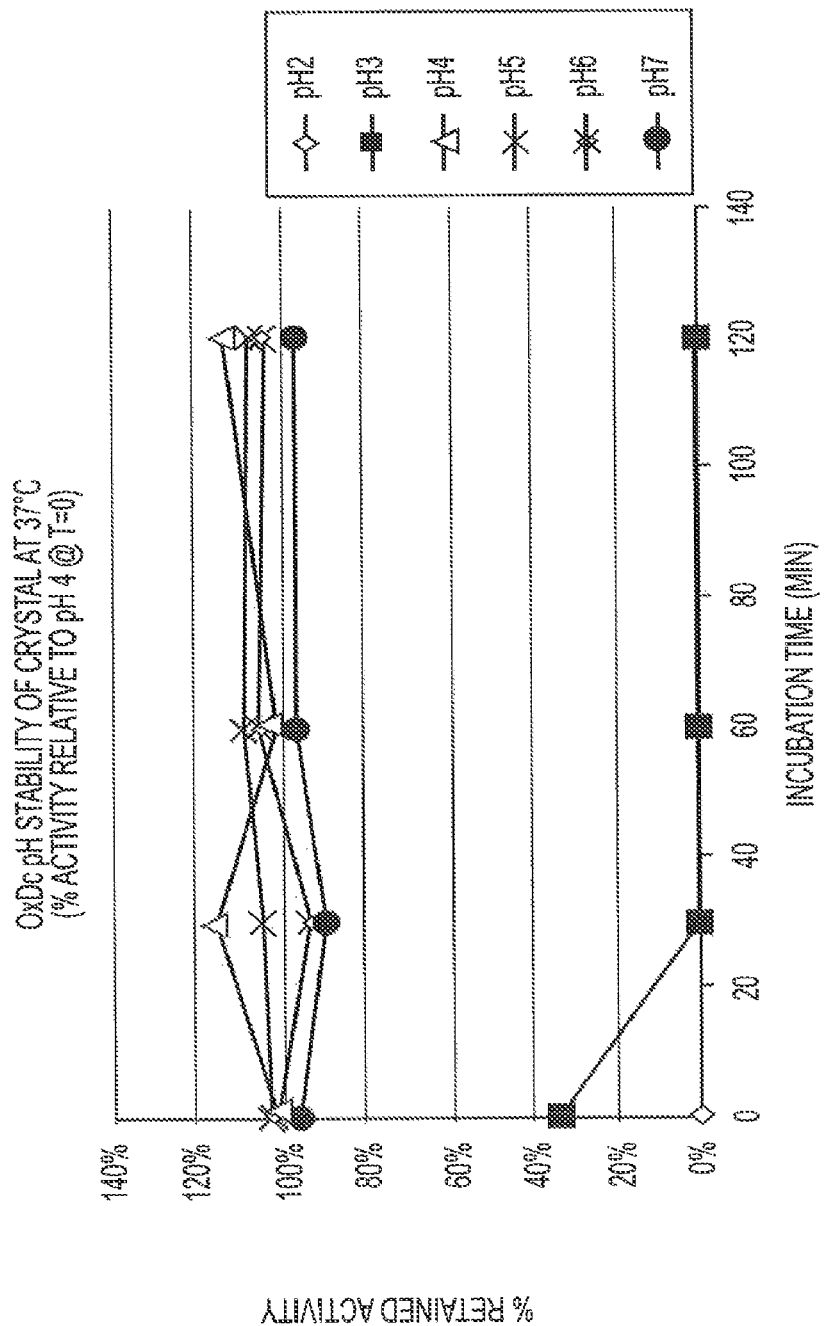
FIG. 2 is the pH stability profile of oxalate decarboxylase crystals.

FIG. 2 shows the percent of retained activity over time for the crystal OXDC. The materials were incubated at the indicated pH for up to two hours followed by pH adjustment to pH 4.0 for the activity measurement.

Example 3

Figure 3:
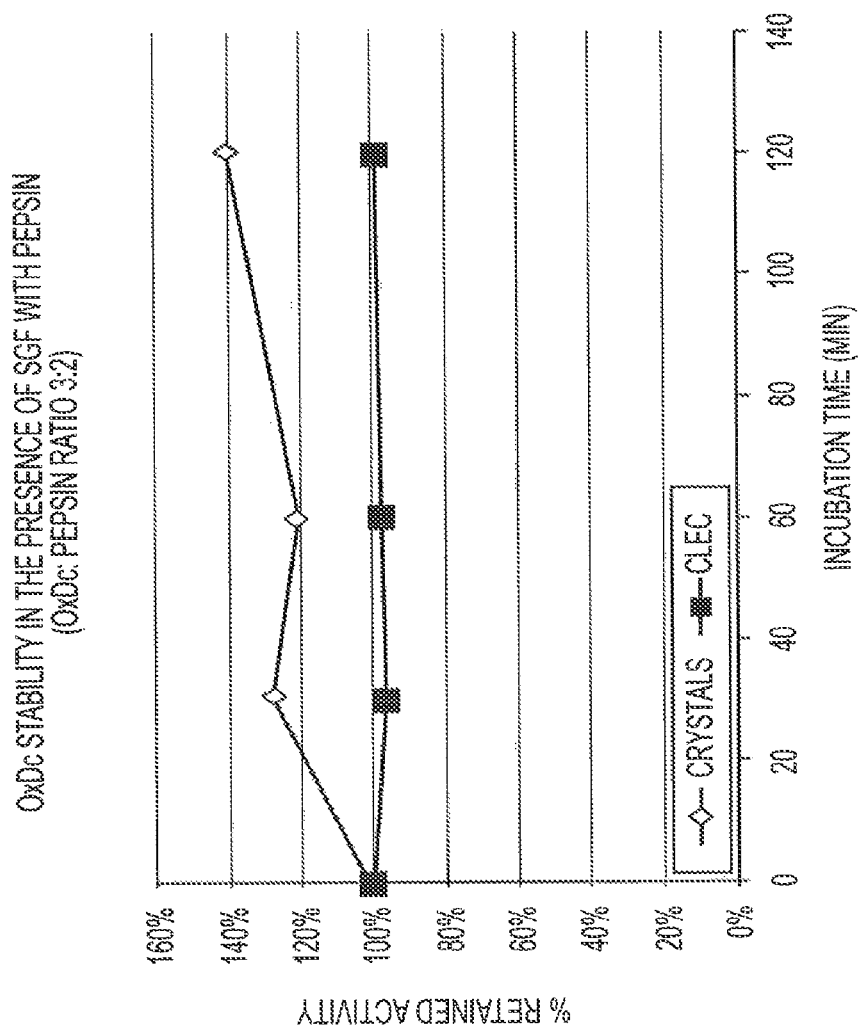
FIG. 3 is the pH stability profile of non cross-linked OXDC crystals vs. cross-linked (CLEC) OXDC in simulated gastric fluid with pepsin at pH 3.7.

FIG. 3 shows the retained enzymatic activity over time of OXDC crystals or CLEC in simulated gastric fluid (SGF: pH 3.7) with pepsin. The stability of OXDC crystals in SGF at pH 3.7 with added pepsin is equal to or better than the CLEC form.

Example 4

Figure 4:
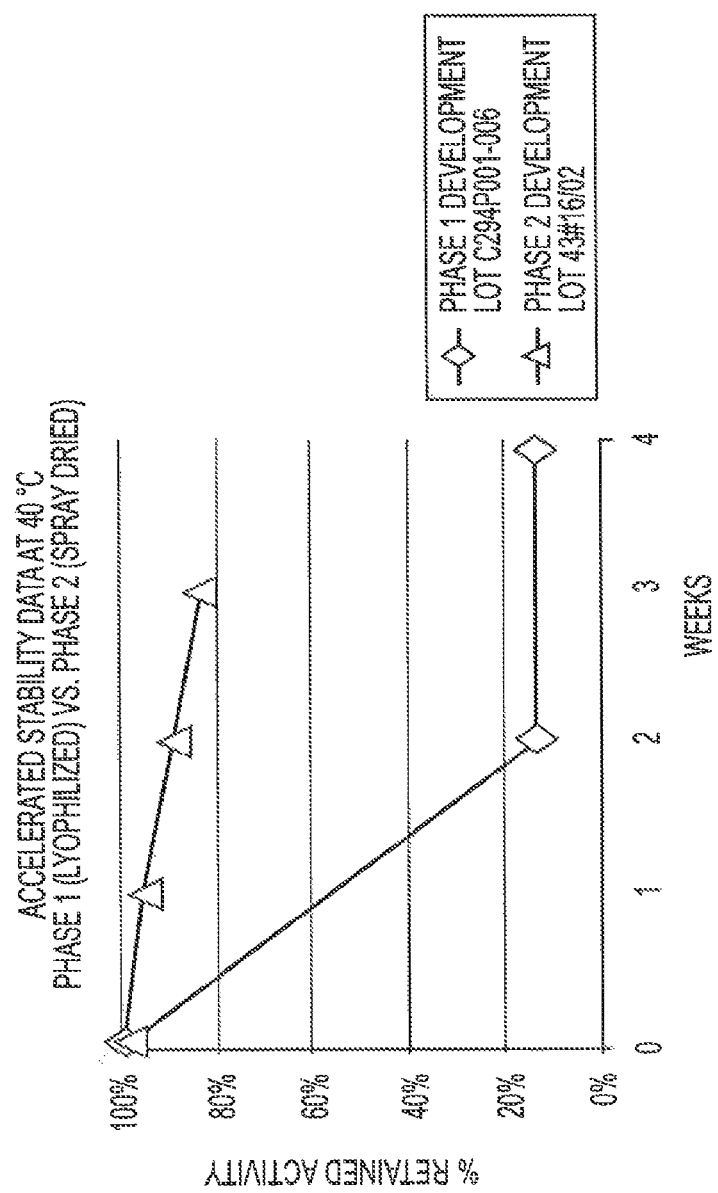
FIG. 4 is the accelerated stability profile for lyophilized vs. spray-dried oxalate decarboxylase crystals.

For spray-drying development, the OXDC crystals were tested in a 40° C./75% RH accelerated development stability study to promote faster degradation and allow rapid screening of multiple formulations and technologies. A comparison of the 40° C. stability for representative lyophilized and spray-dried OXDC crystals is shown in FIG. 4. These data show that the spray drying process selected for the OXDC crystals has a superior accelerated stability profile relative to the lyophilization process.

The spray drying process also results in crystals encased in amorphous spheres of trehalose excipient that prevent the crystals from physically aggregating. This yields crystals with improved power flow characteristics over the lyophilized crystals. Representative data for spray-dried lots are presented in Table 2 and demonstrate "good" flowability per USP while the data for lyophilized crystals demonstrates "very, very poor" flowability per USP.

TABLE 2

Bulk and Tap Densities, and Hausner Ratio (Flowability Index) for Spray Dried Crystals and Lyophilized Crystals

| Entry | Bulk Density (g/mL) | Tapped Density (g/mL) | Hausner Ratio‡ |
|---|---|---|---|
| Spray-dried-Crystals | | | |
| 1 | 0.36 | 0.42 | 1.17 |
| 2 | 0.37 | 0.43 | 1.16 |
| 3 | 0.43 | 0.49 | 1.14 |
| Lyophilized Crystals | | | |
| 4 | 0.35 | 0.69 | 1.97 |

‡The Hausner ratio range for "good" flowability is 1.12 to 1.18: the Hausner ratio for "very, very poor" flowability are values greater than 1.6.

Because the spray-dried crystals are much less compressible than the lyophilized crystals, the spray-dried crystals have improved powder-handling properties and may be used to produce capsules, tablets, sachets or suspensions without the need for compounding and blending operations. This allows a larger number of units to be loaded into capsules, tablets, sachets or suspensions relative to lyophilized crystals and allows less wastage of material when filling capsules, tablets, sachets or suspensions, as well as reduced cost, improved stability and for the delivery of therapeutic doses without a large number of capsules to be used.

Example 5

Figure 5:
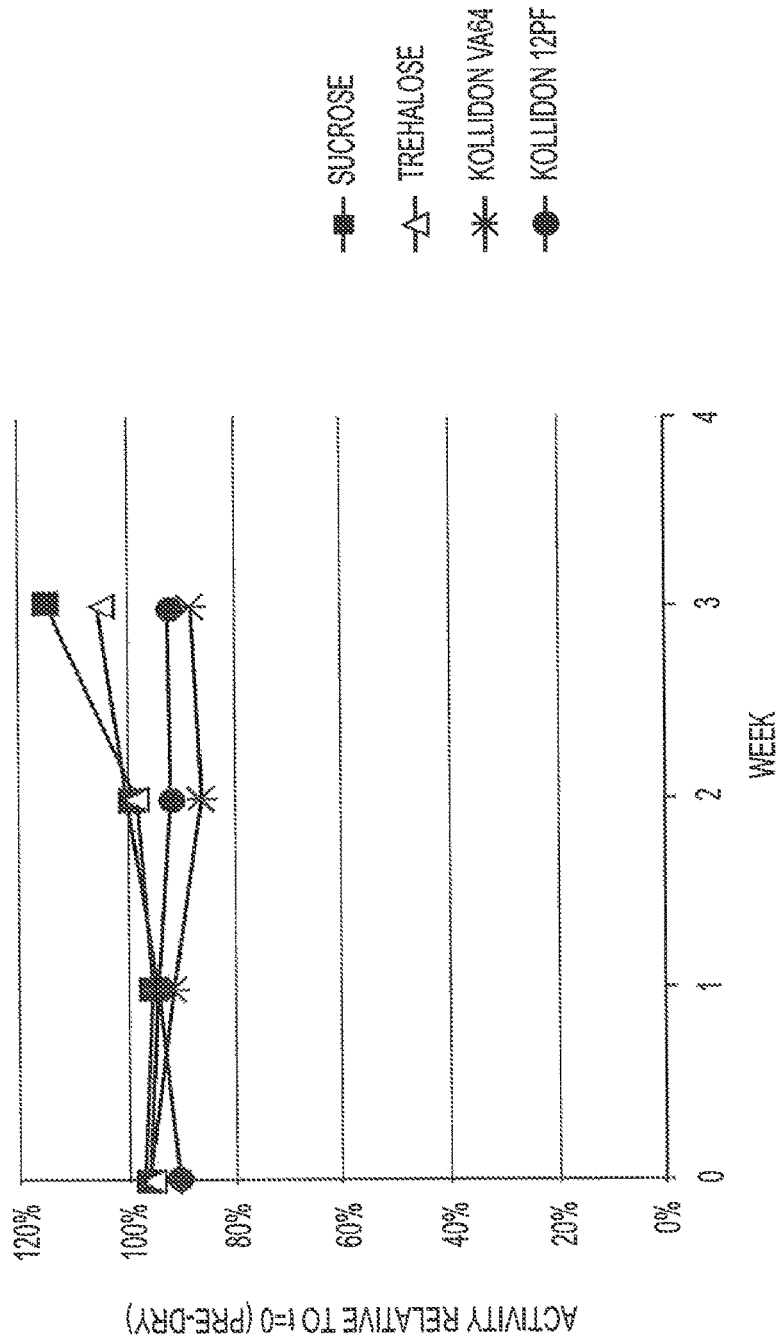
FIG. 5 is the stability data showing activity of OXDC crystals spray-dried with various excipients.

Oxalate decarboxylase spray-dried with each of sucrose, trehalose, copovidone (Kollidon VA64), or providone (Kolloidon 12PF) in separate formulations was tested in a 40° C./75% RH accelerated development stability study for its relative activity to t=0 for three weeks. The results are shown in FIG. 5. Sugar-based excipient exhibited superior stability relative to polymer-based excipients. Spray-dried OXDC with sugar-based excipients also exhibited superior stability relative to spray-dried OXDC with no excipients (data not shown).

A number of embodiments have been described. Nevertheless, it will be understood that various modifications may be made without departing from the spirit and scope of the present disclosure. Accordingly, other embodiments are within the scope of the following claims.

---

What is claimed is:

1. A method of reducing oxalate concentration in the plasma of a subject, the method comprising administering to the subject at least one capsule comprising crystals of spray-dried oxalate decarboxylase comprising the amino acid sequence of SEQ ID NO:1, wherein the thiol moiety at Cys383 is protected by a thiol protecting group, and wherein the crystals have a Hausner ratio of about 1.00 to about 1.59, thereby to reduce oxalate concentration in the plasma of the subject.

2. The method of claim 1, wherein the capsule further comprises an excipient.

3. The method of claim 2, wherein the excipient is a sugar.

4. The method of claim 3, wherein the sugar is a disaccharide or a monosaccharide.

5. The method of claim 4, wherein the sugar is selected from trehalose, sucrose, and glucose.

6. The method of claim 5, wherein the sugar is trehalose.

7. The method of claim 1, wherein the crystals have a Hausner ratio of about 1.00 to about 1.34.

8. The method of claim 7, wherein the crystals have a Hausner ratio of about 1.00 to about 1.25.

9. The method of claim 8, wherein the crystals have a Hausner ratio of about 1.00 to about 1.18.

10. The method of claim 9, wherein the crystals have a Hausner ratio of about 1.12 to about 1.18.

11. The method of claim 8, wherein the crystals have a Hausner ratio of about 1.19 to about 1.25.

12. The method of claim 7, wherein the crystals have a Hausner ratio of about 1.26 to about 1.34.

13. The method of claim 1, wherein the crystals have a Hausner ratio of about 1.34.

14. The method of claim 1, wherein the capsule comprises at least 5,000 U of oxalate decarboxylase crystals.

15. The method of claim 1, wherein the capsule comprises at least 3,000 U of oxalate decarboxylase crystals.

* * * * *